United States Patent
Matloub et al.

(10) Patent No.: US 7,316,817 B2
(45) Date of Patent: Jan. 8, 2008

(54) METHOD AND DEVICE FOR TOPICAL DELIVERY OF THERAPEUTIC AGENTS TO THE SKIN

(75) Inventors: Haitham Matloub, Waukesha, WI (US); Wilfred Lynch, New Glarus, WI (US)

(73) Assignee: New Medical Technologies, Inc., Northbrook, IL (US)

( * ) Notice: Subject to any disclaimer, the term of this patent is extended or adjusted under 35 U.S.C. 154(b) by 278 days.

(21) Appl. No.: 10/751,189

(22) Filed: Jan. 2, 2004

(65) Prior Publication Data

US 2005/0147654 A1  Jul. 7, 2005

(51) Int. Cl.
- *A61F 13/00* (2006.01)
- *A61K 9/70* (2006.01)
- *A61L 15/16* (2006.01)

(52) U.S. Cl. .............. 424/449; 424/443; 424/448

(58) Field of Classification Search ............ 424/449, 424/443, 448, 484–490
See application file for complete search history.

(56) References Cited

U.S. PATENT DOCUMENTS

| | | |
|---|---|---|
| 3,927,669 A | 12/1975 | Glatt |
| 4,838,253 A | 6/1989 | Brassington et al. |
| 4,921,704 A | 5/1990 | Fabo |
| 5,352,508 A * | 10/1994 | Cheong ............... 442/43 |
| 5,445,604 A | 8/1995 | Lang |
| 5,759,560 A | 6/1998 | Dillon |
| 5,895,656 A | 4/1999 | Hirshowitz et al. |
| 5,919,476 A | 7/1999 | Fischer et al. |
| 6,051,747 A | 4/2000 | Lindqvist et al. |
| 6,159,494 A | 12/2000 | Widgerow et al. |
| 6,183,770 B1 * | 2/2001 | Muchin et al. ........ 424/448 |
| 6,284,941 B1 | 9/2001 | Cox et al. |
| 6,326,410 B1 * | 12/2001 | Cheong ............... 521/67 |
| 6,472,581 B1 | 10/2002 | Muramatsu et al. |
| 6,572,878 B1 | 6/2003 | Blaine |
| 2002/0128578 A1 * | 9/2002 | Johnston et al. ....... 602/43 |
| 2004/0138605 A1 | 7/2004 | Sigurjonsson et al. |

FOREIGN PATENT DOCUMENTS

DE            2946553 A *   5/1981

* cited by examiner

*Primary Examiner*—Isis Ghali
(74) *Attorney, Agent, or Firm*—Vedder Price Kaufman & Kamholz; W. Dennis Drehkoff

(57) ABSTRACT

A composite sheet for delivering therapeutic agents to the skin and method of use is disclosed. The composite sheet comprises a flexible porous polymer for holding and releasing the therapeutic agent in a polymer enrobing material. Micro-channels pass through the polymer enrobing material and flexible porous polymer to promote the release of the therapeutic agent. The composite sheet is capable of releasing the therapeutic agent for periods of up to about 14 to about 30 days.

21 Claims, 2 Drawing Sheets

METHOD AND DEVICE FOR TOPICAL DELIVERY OF THERAPEUTIC AGENTS TO THE SKIN

FIELD OF THE INVENTION

This invention relates to an improved device for the delivery of therapeutic agents to the skin and, more specifically, to a device and method of delivering therapeutic agents for the treatment of wounds and scar tissue.

BACKGROUND OF THE INVENTION

While the present invention is directed to a composite sheet for application to the surface of skin for delivering therapeutic agents to the skin, a preferred embodiment will be described showing the delivery of therapeutic agents to the surface of the skin for treating wounds, cuts, burns and scar tissue.

Typically, when the skin is traumatized, cut or burned, scar tissue will form. In some instances the scar tissue may comprise a large area and may become prominent. The scar tissue may discolor or become darkened, become hypertrophic and protrude from the surface of the skin making it more noticeable. It may overgrow the boundaries of the initial area of injury and continue to grow or form a keloid. If the scar tissue happens to cover a joint, the movement of the joint may become restricted and extremely painful.

The severity of the scarring may be affected by many factors including the dimensions of the wound, the blood supply to the wound area, the thickness and color of the skin, and the orientation of the scar. Further, the age of the victim may also affect the scar formation. In younger individuals, this can and may result in larger, thicker scars in comparison to an older individual.

There are several methods available for treating and reducing keloid and hypertrophic scars. Surgical excision has been used for a number of years and has also been proved to be ineffective in a large number of cases due to the recurrence of scar tissue. The surgery requires removal of the scarred skin and rejoining the normal skin in a manner such that the wounded area is less apparent. This type of treatment is fairly expensive, and since it is surgery, there is the possibility of complications.

Dermal abrasion (dermabrasion) is also used to smooth scar tissue by scraping or shaving off the top layers of the skin using surgical devices. The activity is often successful in leveling the irregularities of the surface scars, however, the procedure is painful and multiple treatments may be required. Given that this is a surgical procedure, the concerns raised above are valid and the potential for complications, including hypertrophic and keloid scars still exists.

Other treatments for scar tissue involve the use of injectable fillers such as collagen or fat, which are injected below the depressed scar tissue to elevate it and have it appear to be level with the surrounding skin. Continuous treatments may be required because the results are not always permanent. These agents cannot be used for elevated scars.

Other therapeutic treatments for scar tissue include occlusive dressings, compression therapy, intralesional corticosteriod injections, cryosurgery, radiation therapy, laser therapy and interferon therapy.

Silicone gels in the form of sheets have been widely used in the management of new scar tissue and hypertrophic keloid scarring. The silicone sheets are typically applied with pressure against scar tissue so the formation of hypertrophic scar tissue and attendant coloration can be reduced resulting in a more normal appearance. Typically the silicone sheets are better than traditional bandages because the gel adapts itself to the contours of the body. While the use of silicone dressings may be somewhat effective in the treatment of new scar tissue, the occlusive effects of the silicone sheets may be associated with infection due to the accumulation of microbes on the skin.

U.S. Pat. No. 6,572,878 describes a method for minimizing the appearance of scars comprising the application of a semi-occlusive device to a closed wound on the skin wherein the device comprises one layer of silicone sheet infused with an antioxidant and an antimicrobial. The device is used on the surface of the skin and reapplied daily for up to thirty days.

U.S. Pat. No. 6,472,581 describes a silicone sheet, which is formed by a silicone gel layer with a silicone elastomer layer. The elastomer layer is formed by curing a silicone elastomer composition obtained by adding a silicone cross-linking compound to an addition reaction carrying silicone gel composition.

U.S. Pat. No. 6,159,494 describes a method for treating scars by applying a microporous tape to the scar tissue containing panthenol, which serves as a contact medium for allowing a therapeutic agent to pass there through to the surface of the skin. Typically a hydrating agent is used that is derived from the plant *Bulbine frutesences*.

U.S. Pat. No. 5,919,476 describes a bandage in the form of a reinforced silicone gel sheet for application to scar tissue. The bandage comprises three layers; a tacky skin contacting first layer made from a silicone sheet, a reinforcing second layer comprising a non-liquid permeable mesh fabric support structure having a plurality of holes therethrough and a non-tacky bonding third layer which includes the holes and laminates itself to the first layer, thereby securing the second layer between the first and third layer.

U.S. Pat. No. 5,895,656 describes a gas or gel filled silicone bandage made of silicone sheeting. The flexible silicone sheeting or film contains an interior space that may be filled with dry gas or a hydrophobic gel. Since there is reduced electrical resistance in the scar tissue, the use of the hollow space in the bandage may increase the static electrical field or negative charge applied to the scar which could hasten the inhibitatory healing process for hypertrophic and keloid scars. To improve the electric field within the hollow space, small pieces of Teflon™ sheeting or silicone beads may be inserted in the hollow space.

U.S. Pat. No. 5,759,560 describes a silicone thermal plastic sheeting for scar treatment which has two layers, a first layer of a therapeutic agent to be placed on to the skin and a second backing layer of a thermoplastic polymer bonded to the first layer to provide a thick shape to the material.

U.S. Pat. No. 6,284,941 describes a bandage for treatment of scar tissue comprising a flexible and breathable member having first and second sides with an adhesive located on the first side and a scar treatment pad attached to the first side of the flexible member. The scar treatment pad comprises a layer of silicone elastomer adhesively attached to the center area of the first side of the flexible member so that the adhesive borders are located on lateral sides of the scar treatment pad. The flexible member is non-occlusive.

The foregoing patents describe methods of applying silicone to the surface of skin for treating scar tissue, however, as previously stated, the devices are typically occlusive, or if they are non-occlusive, do not provide for additional application of therapeutic agents. Therefore, there is a need for a device and method for applying therapeutic agents to the skin and treating scar tissue including minimizing the appearance of hypertrophic and keloid scars.

Therefore, it is the object of the present invention to provide a device or composite sheet for delivering therapeutic agents to the surface of the skin.

It is another object of the present invention to provide a device or composite sheet for treating scar tissue.

It is a further object of the present invention to provide a device, which can be applied to the surface of the skin for long periods of time, up to fourteen to thirty days.

It is another object of the present invention to provide a device or composite sheet to be applied to the surface of the skin for preventing and treating scar tissue.

It is another object of the present invention to provide a device or composite sheet to be applied to the surface of the skin for treating acute scars.

It is another object of the present invention to provide a polymer foam material for holding and releasing a therapeutic agent encapsulated in a polymer enrobing material which is in contact with the skin which holds and releases the therapeutic agent on to the skin.

It is another object of the present invention to provide a device or composite sheet to be applied to the surface of the skin for the treatment of non-traumatized skin and for the modulation of the scar forming process through all phases of healing.

It is another object of the present invention to provide a device or composite sheet to be applied to photoaged skin.

It is another object of the present invention to provide a device or composite sheet to be applied to open wounds.

It is another object of the present invention is to provide a composite material containing a plurality of microchannels which pass through a polymer enrobing material and a polymer foam material for holding and releasing a therapeutic agent onto the surface of the skin.

Other objects and advantages will become apparent upon reading the specification of the appendant claims.

SUMMARY OF THE INVENTION

The present invention is a composite sheet that is applied to the surface of the skin for delivering a therapeutic agent to the skin. The composite sheet comprises a flexible porous polymer foam material for holding and releasing therapeutic agent and a polymer enrobing material which is in contact with the skin and encapsulates the polymer foam material and holds and releases the agent. A plurality of microchannels passes through the polymer enrobing material and polymer foam material for holding and releasing the therapeutic agent. The therapeutic agent may be antioxidant, an antibiotic or other medicament or agent that may be topically applied to the skin. The polymer enrobing material is preferably silicone, which is useful for treating scar tissue. A method of treating scar tissue on human skin is also described.

DETAILED DESCRIPTION OF THE PREFERRED EMBODIMENTS

The present invention may be embodied in other specific forms without departing for the spirit or essential attributes thereof, and it is therefore desired that the present embodiment must be considered in all aspects as illustrative and not restrictive, reference being made to the appendant claims rather than to the foregoing description to indicate the scope of the invention.

Figure 1:
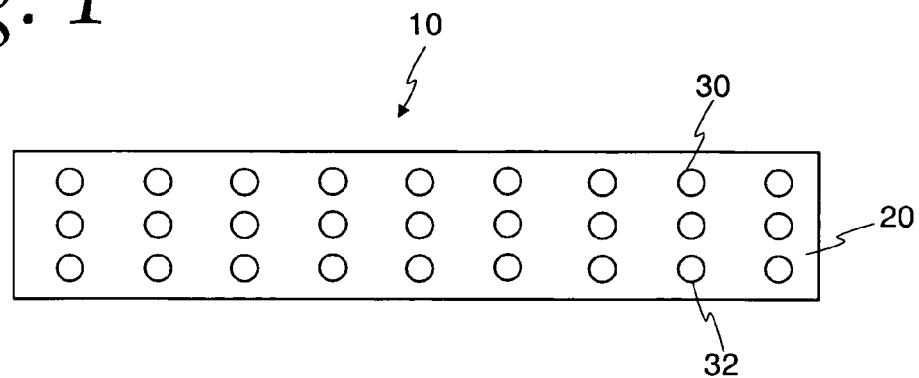
FIG. 1 depicts a top view of the composite sheet material of the present invention.
Figure 2:
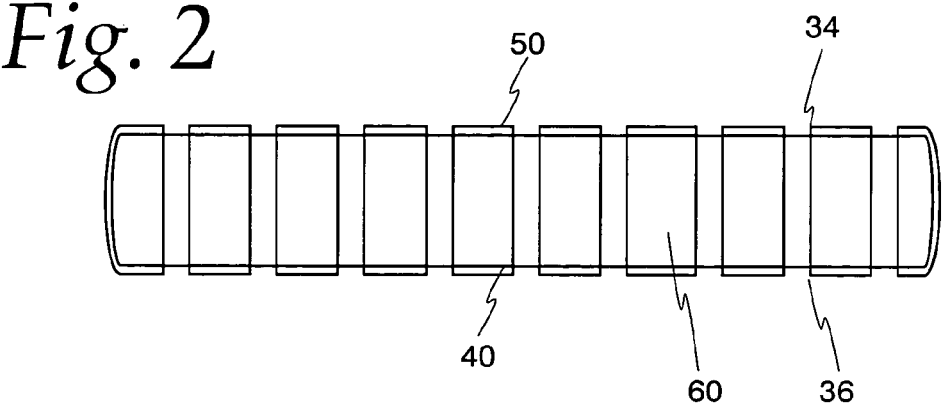
FIG. 2 depicts a length-wise cross-section of the composite sheet material of FIG. 1.
Figure 3:
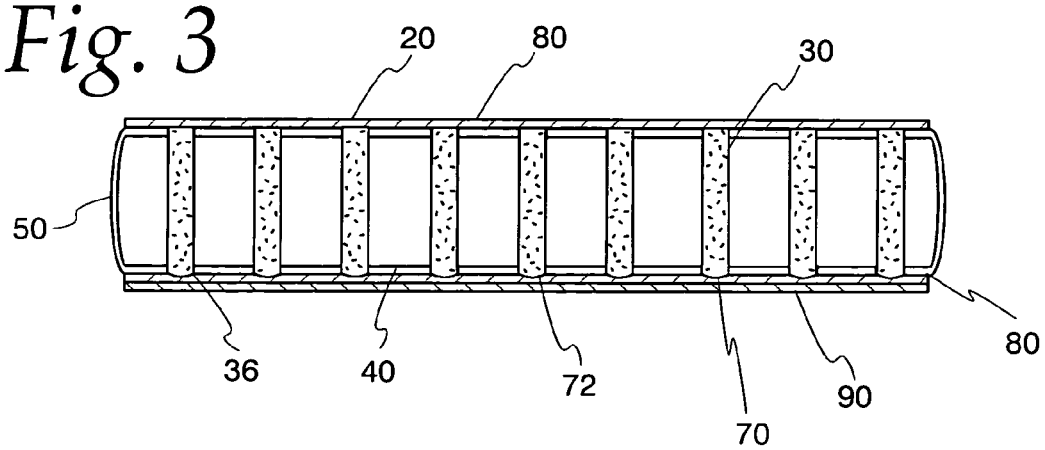
FIG. 3 depicts a cross-section of the composite sheet wherein the therapeutic agents have been added to the micro-channels, completely filling the micro-channels.

As seen in FIG. 1, the composite sheet 10 of the present invention comprises a top or first side 20 showing a plurality of apertures or microchannels 30 in the first side 20. The microchannels 30 run from a first aperture 32 on the top side 20 through a porous passage 34, as seen in FIGS. 2 and 3 to a second aperture 36, exiting the second side 40 of the composite sheet of the present invention.

The microchannels 30 pass through a polymer enrobing material 50 which contacts the skin on the second side of the composite sheet and encapsulates a flexible porous polymer foam material 60 that holds and releases a therapeutic agent 70. The polymer enrobing material 50 preferably is a silicone gel or silicone elastomer that is prepared in the form of a sheet. The silicone is soft, durable and of a medical grade. It is impregnated with a therapeutic agent 70, which also passes through the microchannel 30 and into the flexible porous foam material 60. The polymer enrobing material 50 may also be a hydrogel or other suitable material such as ethylene-vinyl acetate and polyurethane elastomers.

Figure 5:
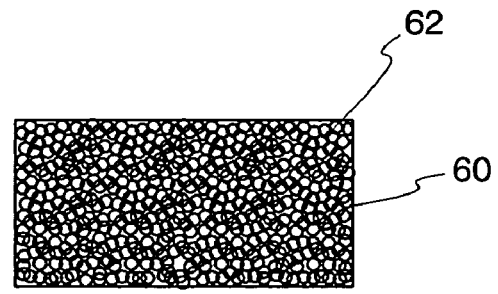
FIG. 5 depicts the open cell structures of the porous polymer foam material.

The flexible porous polymer 60 foam material may be a polymer foam that is flexible, with open foam cells 62 of about 200 to about 300 microns diameter to allow for the holding and releasing of a therapeutic agent, as shown in FIG. 5. Indeed, the open cells of the polymer foam of the present invention should be of a sufficient size to hold an amount of therapeutic active agent so it can be released onto the skin through the polymer enrobing material for as much as about 14 to about 30 days. The polymer foam material may be selected from the group consisting of polyurethane, polyvinylacetate, polyvinyl alcohol (PVA), polyethylene and medical grade silicone. Preferably hydrophilic polyurethane is utilized. It is available from the following sources: Rynel, Inc. Boothbay, Maine and Lendell Inc. (LMI) St. Charles, Mo.

The thickness of its composite sheet is not critical, however, it typically may have a thickness ranging from about 1 to about 1.5 mm. The flexible polymer foam may have a thickness of about 0.8 to about 0.9 mm.

FIG. 2 shows a cross-sectional view of FIG. 1 wherein the microchannels 30 are formed, passing through the first side 20 to second side 40 of the composite sheet material via first aperture 32, porous passage 34 to second aperture 36. The enrobing polymer 50 is shown encapsulating flexible porous foam 60.

FIG. 3 shows a composite sheet that has microchannels 30 filled with a therapeutic agent 70. The microchannels are filled completely so that the therapeutic agent 70 reaches the second aperture 36. The therapeutic agent may flow downward past the second aperture 36 to collect in bulge 72.

If needed, a thin polymer membrane liner 80 may be utilized to cover apertures 32 and 36 on first and second sides 20 and 40, respectively. The liner can be any polymeric material that could be removably attached to the first and second sides 20 and 40 of the composite sheet material. The polymeric material may be selected from the group consisting of polyethylene terephthalate, polyethylene terephthalate amorphous, polyethylene terephthalate glycol (glycol modifiers of polyethylene terephthalate), polyvinyl chloride, polypropylene, polystyrene, and polyethylene. Preferably polypropylene is used.

Further, a rigid polymer strip 90 may be applied to either side of the composite sheet, however, preferably it is applied on the second side 40 to cover the polymer liner 80 over apertures 32 and 36. The strip 90 may or may not have raised protrusions 92 to aid the blockage of the therapeutic agent 70 in the microchannels 30, preferably on the second side that contacts the skin of the patient. The strip 90 is removably attached from the first and second sides 20 and 40 prior to application of the composite sheet to the skin. The strip 90 is shown on second side 40 in FIGS. 3 and 4.

Figure 4:
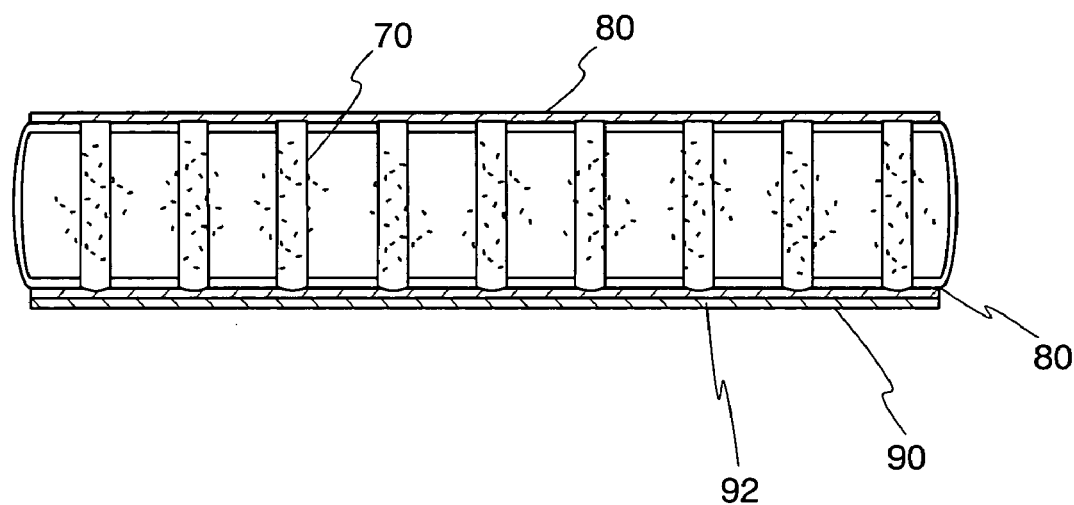
FIG. 4 depicts a cross-section of the composite sheet wherein the therapeutic material has been added to the microchannels and has been dispersed into the porous polymer foam material and polymer enrobing material.

FIG. 4 shows the therapeutic agent 70 filling or partially filling the open cells of the polymer foam 60 into the flexible polymer foam 60 and polymer enrobing material 50 from the microchannels 30. The therapeutic agent easily migrates throughout the foam (due to the open-cell foam properties) and enrobing material. The open foam cells 62 are filled, or partially filled with the therapeutic agent 70 and are ready to release the therapeutic agent into the skin when the strip 90 and liner 80 are removed and the composite sheet is applied to the skin. Typically, when silicone is used as the polymer enrobing material, it will adhere to its skin surface because of its tacky nature.

If necessary, or possibly if other enrobing materials are utilized in the present invention, the appropriate adhesive materials, tapes, bandages, etc. may be used in conjunction with the composite strip to attach the strip to the skin.

FIG. 5 closely shows the open cell 62 of the flexible polymer foam 60.

The therapeutic and non-therapeutic agents which may be utilized with the polymer enrobing material and flexible polymer foam material of the present invention may be any agent that would be suitable for topical application to the skin. For convenience, the term "therapeutic agent" is utilized herein with no intention to be limitative. Hence this device can be used to treat, modulate or prevent various cosmetic or non-cosmetic conditions, diseases, neoplasms, blemishes, photoaged skin, biologic deficiencies, nutritional deficiencies, wounds and scars. More than one therapeutic agent may be utilized. These agents may be drugs, vitamins, minerals, manufactured substances, interferon, hormones, steroids, natural products or a combination of these and others. For example, antioxidants, and antimicrobials may be loaded into microchannels 30 for release into the flexible foam material 60 and enrobing material 50 for release onto the skin surface. Antioxidants are capable of inhibiting oxidation and when used on the surface of the skin, may prevent fibrosis and decreasing free radical formation when treating wounds and scar tissue. Vitamin E (alpha-tocopherol) is a preferred antioxidant for use in the composite sheet, however, other antioxidants or vitamins may also be utilized, such as Vitamin C, ascorbyl palmitate, butylated hydroxyanisole, butylated hydroxytoluene and sodium bisulfate or therapeutic oils and plant or animal extracts such as aloe, emu oil, lavender oil, and rosehip oil. The amount of the antioxidant or other agent used is an amount sufficient to partly or completely fill the open foam cells 62 so that the antioxidant would be released in a time period ranging from zero to about 14 to about 30 days onto or into the skin. The amount cannot exceed the concentration that will go into and remain in the solution with silicone, if silicone is used as the polymer enrobing material. If other materials are used as the polymer enrobing material, they will determine the amount of therapeutic agent or additive. The amount of antioxidant that may be used in the present invention, when silicone is used as the enrobing material may typically range from about 1% to about 10% by weight of the sheet, with about 1.5% to about 5% being preferred. The composite sheet of the present invention allows for the application of medication to the skin or scar tissue for long periods of time without the need for changing dressings.

Antimicrobials may also be loaded or filled into the microchannels of the present invention. Both the antimicrobials and antioxidants may reach the skin through the microchannels 30 or through the flexible porous foam material 60 and polymer enrobing material 50. Both of these materials may impregnate or be impregnated into the silicone or other enrobing material for release onto or into the skin. The preferred antimicrobial used as a therapeutic agent is polymixin B sulfate. Other antimicrobials, antivirals, antibiotics, antifungals, and antineoplastic agents may also be used in the present invention if they are safe for topical application to the skin and are compatible with other ingredients of the composite sheet material. Examples of these include fusidic acid, bacitracin zinc, gramicidin, siliver in various forms and compounds, aminoglycosides, and sulfa based antibiotics such as silver sulphadine.

The antimicrobials allow the composite sheet to remain on the surface of the skin for extended periods of time because they inhibit bacterial growth and treat infections.

Analgesics can be added to this device for the treatment, control or modulation of painful conditions of the skin or other organs and body systems. Similarly, agents for treating global endocrine and non-endocrine deficiencies can be delivered with this device through the skin for management of a variety of conditions, diseases or deficiencies, for example, platelet derived growth factor.

Steroids, for example, corticosteroids selected from the group consisting of triamcinolone and dexamethasone, may also be delivered to the skin by the present invention.

The composite sheet of the present invention may be manufactured by the following steps: (1) pouring the enrobing material, for example, silicone into a mold, (2) adding the flexible porous foam material to the silicone or enrobing material, (3) adding additional silicone or enrobing material to cover the flexible porous foam, (4) curing the silicone mixture or enrobing material by the application of heat, (5) removing the composite sheet material from the mold, (6) cutting holes or apertures through the composite sheet material to form a plurality of microchannels throughout the material by conventional means, (7) loading the microchannels with one or more therapeutic agent, (8) applying a polymer liner to cover the apertures containing the therapeutic agent, (9) covering the liner with a rigid polymer strip for securely retaining the therapeutic agent in the microchannels of the composite sheet.

For the application to the patient, the composite sheet should be applied to the site to be treated on the skin, for example, scar tissue, wounds, etc. The sheet may be secured if the enrobing material is not sufficiently tacky or sticky for adhesion to the skin. The-composite sheet does not have to be applied with much pressure or too tightly, for skin irritation may result. The composite sheet material may stay on the skin of the patient for long periods of time, for example, from about 14 to about 30 days without reapplication. The antimicrobial agent is typically used in addition with a second therapeutic agent to prevent infection at the site. Nevertheless, the treatment site can be washed with soap and water around the composite sheet to lessen the chances of infection.

Although this invention has been described with reference to a preferred embodiment, obvious modifications and alterations of the invention may be made without departing from the spirit and scope of the invention. The preferred application of the present invention is for the treatment of scar tissue, however, the composite sheet of the present invention may be used for delivering various therapeutic agents to the skin.

What is claimed is:

1. A composite sheet, which is applied to the surface of skin for delivering a therapeutic agent to the skin comprising:
   a flexible porous polymer open cell foam material for holding and releasing the therapeutic agent,
   a polymer enrobing material which is in contact with the skin and encapsulates the polymer open cell foam material and holds and releases the agent, and
   a plurality of microchannels passing through the polymer enrobing material and polymer open cell foam material for holding and releasing the agent, wherein the microchannels are loaded with therapeutic agent, and
   the therapeutic agent is delivered from the microchannels into the porous polymer open cell foam material and polymer enrobing material for release to the skin.

2. The composite sheet according to claim 1 wherein the sheet is capable of releasing the therapeutic agent for a period of about 0 to about 14 days.

3. The composite sheet according to claim 1 wherein the porous polymer open cell foam material has open face pores for holding and releasing the therapeutic agent having a diameter of about 200 to about 300 microns.

4. The composite sheet according to claim 1 wherein the porous polymer open cell foam material is selected from the group consisting of polyurethane, polyvinylacetate, polyvinyl alcohol, polyethylene, and silicone.

5. The composite sheet according to claim 1 wherein the polymer enrobing material which encapsulates the porous polymer open cell foam material is selected from the group consisting of silicone, hydrogels, ethylene-vinyl acetate and polyurethane elastomers.

6. The composite sheet according to claim 1 wherein the sheet has a first side and a second side which contacts the skin with the microchannels, passing therethrough for holding and releasing the therapeutic agent into the porous polymer open cell foam material and polymer enrobing material for release to the skin.

7. The composite sheet according to claim 6 having a removable rigid polymer strip, which is applied to the first and second sides for retaining the therapeutic agent in the microchannels prior to application of the sheet to the skin.

8. The compound sheet according to claim 1 wherein the therapeutic agent is selected from the group consisting of therapeutic oils, plant extracts, animal extracts, drugs, vitamins, minerals, hormones, antioxidants, Vitamin E, Vitamin C, emu oil, aloe vera, silver sulphadiazine, polymixine B, fusidic acid, platelet-derived growth factor, corticosterioids and interferon.

9. The composite sheet according to claim 1 wherein the composite sheet is capable of releasing the therapeutic agent for a period of about 14 to about 30 days.

10. The composite sheet according to claim 1 wherein the porous polymer open cell foam material is polyurethane, and wherein said polyurethane is hydrophilic.

11. The composite sheet according to claim 1 wherein the composite sheet is capable of releasing the therapeutic agent for a period of about 30 days.

12. A method of delivering a therapeutic agent to the skin comprising loading one or more therapeutic agents into microchannels passing through a flexible porous polymer open cell foam material, and a polymer enrobing material which is in contact with the skin and encapsulates the flexible porous polymer open cell foam material so that the therapeutic agent is dispersed from the microchannels into the flexible porous polymer open cell foam and polymer enrobing material, and thereby releasing the therapeutic agent to the skin.

13. The method according to claim 12 wherein the porous polymer open cell foam material is selected from the group consisting of polyurethane, polyvinylacetate, polyvinyl alcohol, polyethylene, and silicone.

14. The method according to claim 12 wherein the polymer enrobing material which encapsulates the porous polymer open cell foam material is selected from the group consisting of silicone, hydrogels, ethylene-vinyl acetate and polyurethane elastonaers.

15. The method according to claim 12 wherein the sheet has a first side and a second side which contacts the skin with the microchannels, passing therethrough forming an area for holding and directly releasing the therapeutic agent onto or into the skin and into the porous polymer open cell foam material and polymer enrobing material for subsequent release to the skin.

16. The method according to claim 12 wherein the plurality of microchannels pass through the polymer open cell foam material and polymer enrobing material for dispersing the therapeutic agent for distribution on the skin.

17. The method according to claim 12 wherein the therapeutic agent is selected from the group consisting of therapeutic oils, plant extracts, animal extracts, drugs, vitamins, minerals, hormones, antioxidants, Vitamin E, Vitamin C, emu oil, aloe vera, silver sulphadiazine, polymixine B, fusidic acid, platelet-derived growth factor, corticosterioids and interferon.

18. A composite sheet, which is applied to the surface of skin for delivering a therapeutic agent to the skin comprising:
   a flexible porous polymer open cell foam material for holding and releasing the therapeutic agent,
   a polymer enrobing material which is in contact with the skin and encapsulates the polymer open cell foam material and holds and releases the agent, and
   a plurality of microchannels passing through the polymer enrobing material and polymer open cell foam material for holding and releasing the agent, wherein the microchannels are loaded with therapeutic agent,
   the therapeutic agent is delivered from the microchannels into the porous polymer open cell foam material and polymer enrobing material for release to the skin, and
   the therapeutic agent is released from the microchannels onto the skin.

19. The composile sheet according to claim 18 wherein the sheet is capable of releasing the therapeutic agent for a period of about 0 to about 14 days.

20. The composite sheet according to claim 18 wherein the sheet is capable of releasing the therapeutic agent for a period of about 0 to about 30 days.

21. The composite sheet according to claim 1 wherein the sheet is capable of releasing the therapeutic agent for a period of about 0 to about 30 days.

* * * * *